US012128163B2

United States Patent
Signorino et al.

(10) Patent No.: US 12,128,163 B2
(45) Date of Patent: Oct. 29, 2024

(54) AIR TREATMENT APPARATUS FOR A DOMESTIC APPLIANCE

(71) Applicant: emz-Hanauer GmbH & Co. KGaA, Nabburg (DE)

(72) Inventors: Manfredi Signorino, Wackersdorf (DE); Martin Brabec, Nabburg (DE); Georg Spiessl, Altendorf (DE); Günter Zühlke, Stulln (DE)

(73) Assignee: emz-Hanauer GmbH & Co. KGaA, Nabburg (DE)

( * ) Notice: Subject to any disclaimer, the term of this patent is extended or adjusted under 35 U.S.C. 154(b) by 599 days.

(21) Appl. No.: 17/469,271

(22) Filed: Sep. 8, 2021

(65) Prior Publication Data
US 2022/0072190 A1 Mar. 10, 2022

(30) Foreign Application Priority Data

Sep. 10, 2020 (DE) .......................... 102020123643.3

(51) Int. Cl.
*A61L 9/20* (2006.01)
(52) U.S. Cl.
CPC .......... *A61L 9/205* (2013.01); *A61L 2209/11* (2013.01); *A61L 2209/12* (2013.01)
(58) Field of Classification Search
CPC .......... A61L 9/205; A61L 2209/11–12; A61L 2202/11; A61L 2202/122; A61L 2209/111; A61L 2202/121; B60H 3/00; F24F 3/16; F24F 1/02; F24F 11/65; A47F 3/0408; A47F 3/0443; A47L 15/42; A47L 2501/10; A47L 2501/16; A47J 37/0754; A47J 39/003; F24H 9/0073; F25D 17/04–06; F25D 23/12; F25D 2317/06; D06F 39/00; B67D 1/145; B67D 1/1438; B67D 1/1444; F01L 31/00; F01L 2013/103; F01L 2313/00; F01L 7/06
USPC ....................................... 422/186.3
See application file for complete search history.

(56) References Cited

U.S. PATENT DOCUMENTS

| 9,803,910 B2* | 10/2017 | Kim .......................... B01J 23/72 |
| 11,022,361 B2* | 6/2021 | Buzzi .................... F25D 17/065 |
| 2005/0265890 A1* | 12/2005 | Yang ....................... D06F 58/20 68/5 R |

(Continued)

FOREIGN PATENT DOCUMENTS

| CN | 103338792 | 10/2013 |
| CN | 103983069 | 8/2014 |

(Continued)

OTHER PUBLICATIONS

Office_Action_CN_114159919_A (Year: 2023).*
(Continued)

*Primary Examiner* — Harry D Wilkins, III
*Assistant Examiner* — John Lee
(74) *Attorney, Agent, or Firm* — Sheridan Ross P.C.

(57) ABSTRACT

The invention relates to an air treatment apparatus for a domestic appliance, with at least one air flow device being provided, by means of which an air flow into and/or out of the air treatment apparatus can be generated, the air flow passing through at least one treatment device, and the air treatment apparatus having a closure device by means of which the air treatment apparatus can be sealingly closed.

14 Claims, 11 Drawing Sheets

(56) References Cited

U.S. PATENT DOCUMENTS

| | | | | |
|---|---|---|---|---|
| 2007/0131259 | A1* | 6/2007 | Classen | A47L 15/4276 |
| | | | | 134/25.2 |
| 2016/0193374 | A1* | 7/2016 | Sarphati | A61L 2/24 |
| | | | | 422/114 |
| 2016/0303272 | A1* | 10/2016 | Koo | F24F 8/192 |
| 2017/0197004 | A1* | 7/2017 | Kim | A45C 15/00 |
| 2017/0216475 | A1 | 8/2017 | Park et al. | |
| 2018/0104374 | A1* | 4/2018 | Kim | A61L 9/205 |
| 2020/0345887 | A1* | 11/2020 | Kim | D06F 58/20 |

FOREIGN PATENT DOCUMENTS

| | | | | |
|---|---|---|---|---|
| CN | 107997721 A | * | 5/2018 | A47L 15/42 |
| CN | 213454440 | | 6/2021 | |
| WO | WO-2013079462 A1 | * | 6/2013 | A47L 15/4276 |

OTHER PUBLICATIONS

Office_Action_KR_20220034692_A (Year: 2023).*
Official Action for Germany Patent Application No. 102020123643. 3, dated Aug. 5, 2021, 9 pages.
Official Action (with English translation) for China Patent Application No. 202111059879.3, dated Sep. 29, 2023, 10 pages.
Official Action (with English translation) for China Patent Application No. 202111059879.3, dated Jun. 7, 2023, 12 pages.
Official Action for China Patent Application No. 202111059879.3, dated May 6, 2024, 4 pages.

\* cited by examiner

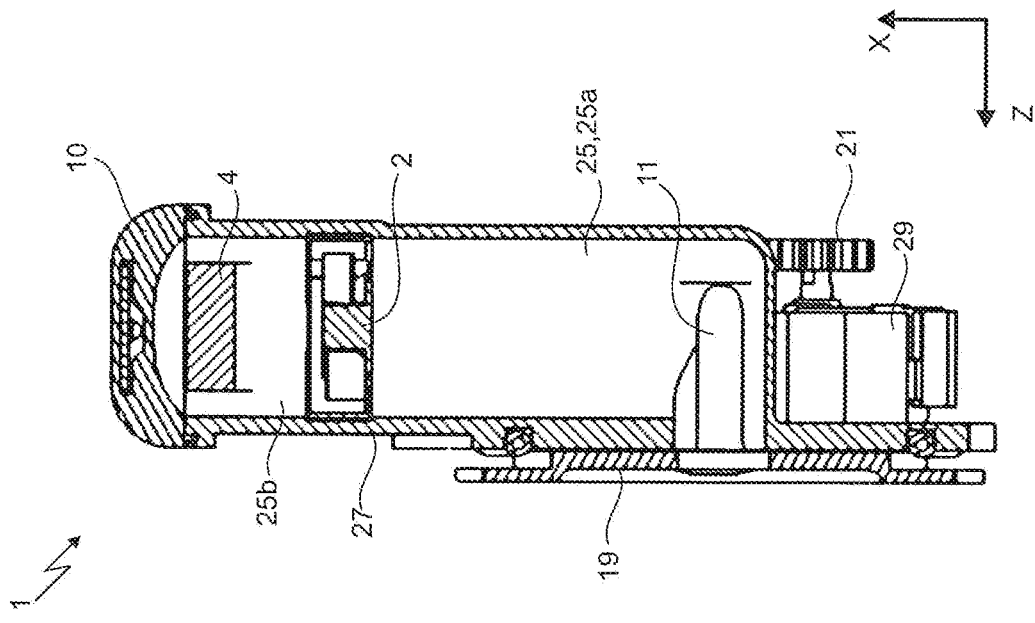
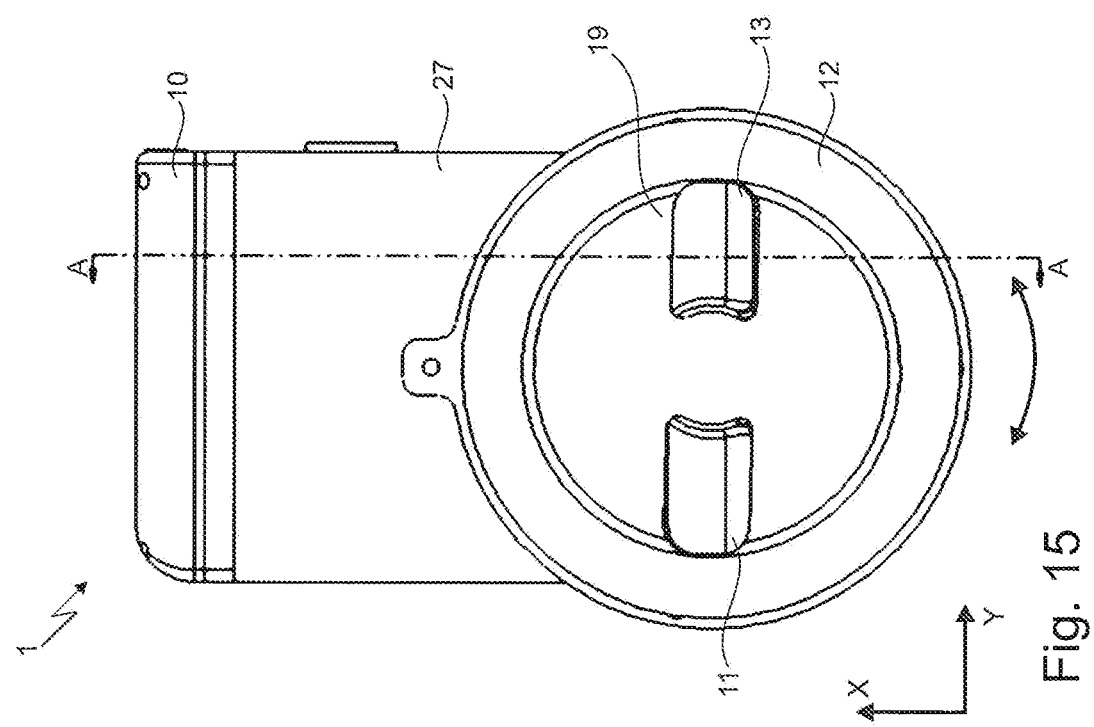

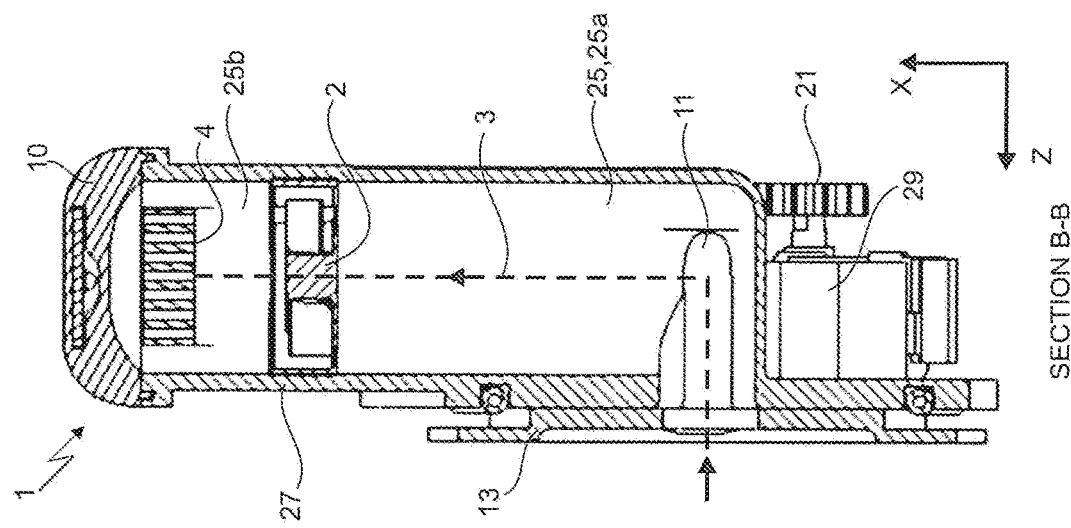
Fig. 19 SECTION B-B SCALE 2:1
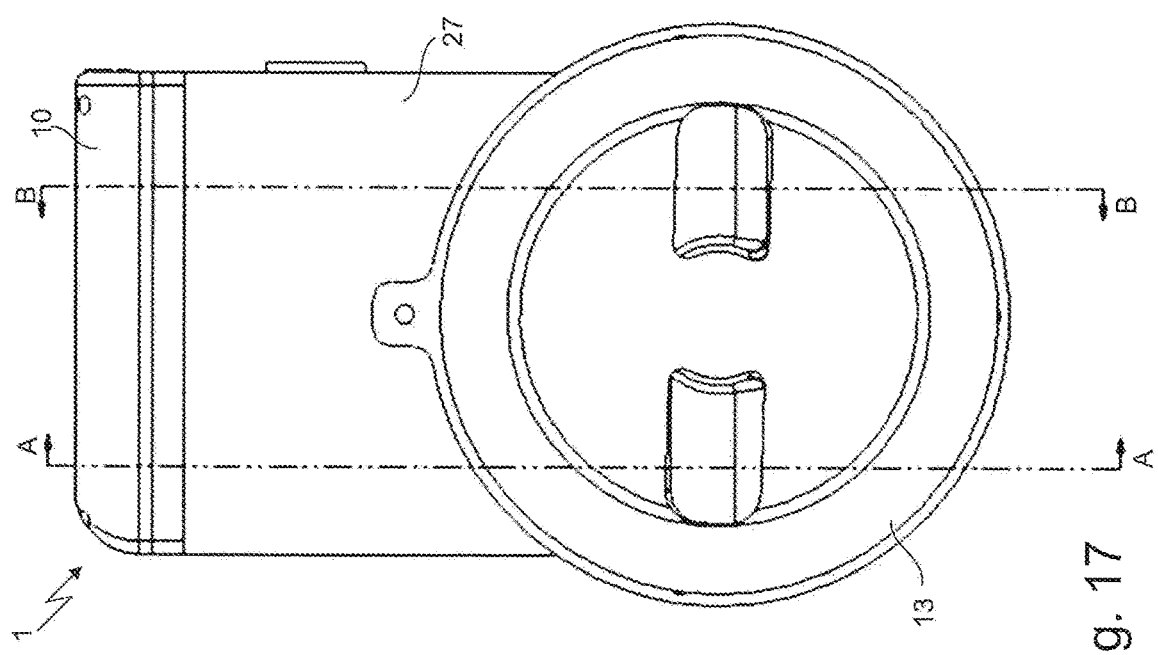
Fig. 17
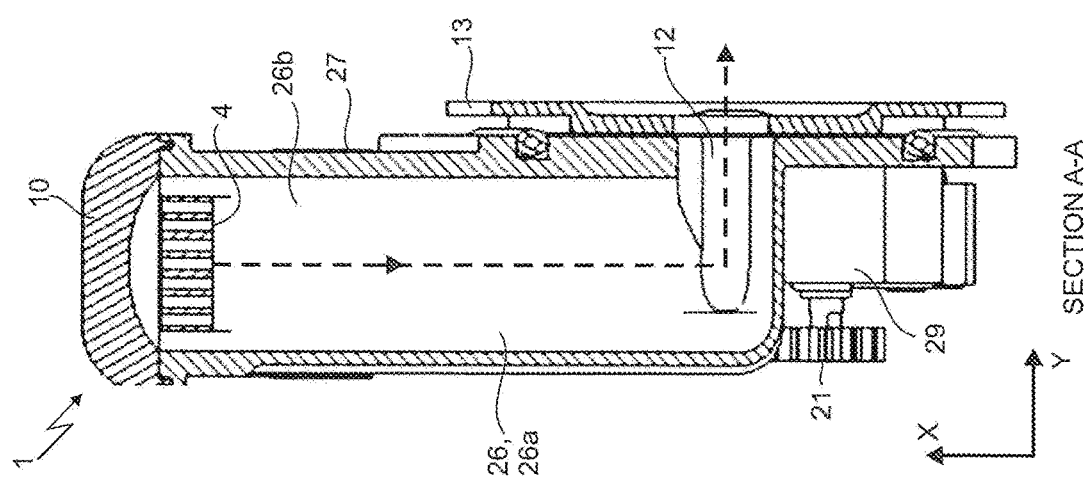
Fig. 18 SECTION A-A SCALE 2:1

AIR TREATMENT APPARATUS FOR A DOMESTIC APPLIANCE

CROSS-REFERENCE TO RELATED APPLICATIONS

This application claims the benefit of German Patent Application No. 10 2020 123 643.3 filed Sep. 10, 2020, the entire contents of which are hereby incorporated herein by reference.

FIELD

The invention relates to an air treatment apparatus for a domestic appliance and to a domestic appliance with an air treatment apparatus comprising a housing and a container device provided therein.

BACKGROUND

Such domestic appliances can be dishwashers or washing machines, for example. In such a case, the container device would be a tub in which the items to be washed and the washing liquid are located. Such a domestic appliance could also be a refrigerator or freezer, for example, and the container device would accordingly be the cooling space in which the items to be cooled are located.

As the operating time increases, it is often desirable for the air in the container device to be treated. Microorganisms present in the air—such as viruses, bacteria, yeasts and moulds—can endanger human health, contaminate raw materials and spoil food. Furthermore, the air can contain gases, liquids and solids which leave an unpleasant odour. A permanent opening for air exchange is often not desirable, however, since for example washing liquid can leak out of the container device. In the case of a domestic appliance in the form of a refrigerator, the cooling power can be affected by a permanent opening, or undesired contaminants can also enter the container device.

SUMMARY

The object of the present invention is to provide an air treatment apparatus for a domestic appliance which overcomes the disadvantages mentioned. Another object of the invention is to provide a domestic appliance with an air treatment apparatus.

This object is achieved by the subject matter of claims 1 and 9. The dependent claims comprise preferred embodiments.

According to the invention, an air treatment apparatus for a domestic appliance is provided, with at least one air flow device being provided, by means of which an air flow into and/or out of the air flow device can be generated, the air flow passing through at least one treatment device, and the air treatment apparatus having a closure device by means of which the air treatment apparatus can be sealingly closed.

The domestic appliance advantageously comprises a housing and a container device provided therein. The air treatment apparatus can preferably be arranged on or in the housing of the domestic appliance. Advantageously, by means of the closure device, the air treatment apparatus can be sealingly closed off or separated from the container device. Advantageously, an air flow into and/or out of the container device can be generated by means of the at least one air flow device. The sealing closure is advantageously present only with respect to the container device. The air treatment apparatus can advantageously be activated only when required. In a non-activated state, the air treatment apparatus is separated from the container device or closed off from it. Accordingly, the container device is also closed off or isolated accordingly. Neither washing liquid nor cooling power can thus inadvertently escape from the container device. Furthermore, the advantageous sealing closure can protect the air flow device as well as the treatment device from the washing liquid, for example. The air in the container device is treated, i.e. cleaned and/or disinfected, by the at least one treatment device.

According to a preferred embodiment, the treatment device comprises a passage channel for the air flow, a radiation source device and a photocatalysis device. The radiation source device preferably emits electromagnetic radiation. Preferably, the photocatalysis device can be exposed to at least part of the electromagnetic radiation to produce a photocatalytic reaction.

According to a preferred embodiment, the photocatalysis device comprises at least one photocatalytic material. The photocatalysis device preferably comprises a photocatalysis surface which comprises at least one photocatalytic material. The photocatalytic material is preferably integrated in the photocatalysis surface. At least the photocatalysis surface preferably consists at least partially of at least one photocatalytic material. Advantageously, the photocatalysis surface of the photocatalysis device comprises portions consisting of a photocatalytic material. Preferably, at least the photocatalysis surface of the photocatalysis device consists entirely of a photocatalytic material. The photocatalysis surface is preferably exposed to the electromagnetic radiation from the radiation source device.

The photocatalytic material of the photocatalysis device is preferably a semiconductor. Semiconductors are usually described by the so-called band model and comprise a conduction band and a valence band, which are energetically separated from one another by the so-called band gap. The size of the band gap varies with the corresponding individual semiconductor material. The valence band and the conduction band are occupied by electrons according to the Fermi distribution. Accordingly, at zero temperature, the valence band is occupied and the conduction band is unoccupied. An incident photon can create an electron-hole pair if the energy of the photon is greater than or equal to the energy difference in the band gap. The mobile electrons in the conduction band can advantageously result in a chemical or photocatalytic reaction on the surface of the photocatalytic material. A particle in the air is advantageously reduced in this case. Such a particle can preferably be a molecule, an ion or an atom. This reduction can already change the chemical properties of certain components so that they no longer cause an unpleasant odour or can be removed more easily, for example by washing. Furthermore, the chemical or photocatalytic reaction can generate free radicals. Free radicals are molecules, ions or atoms with an unpaired electron and are highly reactive. These free radicals can advantageously react with the undesired microorganisms and gases in the air and kill them or convert them into other gases. The air is thus cleaned of undesired microorganisms and undesired gases, which can cause unpleasant odours. According to a preferred embodiment, the photocatalytic material is titanium (IV) oxide, or titanium dioxide, $TiO_2$.

According to a further advantageous embodiment, the radiation source device comprises at least one radiation source. The at least one radiation source is preferably a light-emitting diode (LED). The radiation source device advantageously emits electromagnetic radiation with a wavelength of less than 400 nm. The radiation source device advantageously emits UV radiation. The at least one radiation source is preferably a UV LED. The emitted electromagnetic radiation, preferably in the form of UV radiation, strikes the photocatalysis device or the photocatalysis surface and causes the above-described photocatalytic reaction. In an advantageous use of titanium dioxide $TiO_2$, irradiation with UV radiation results in the generation of an electron-hole pair and the described chemical or photocatalytic reaction. Titanium dioxide can preferably remove natural and artificial impurities in air and water by irradiation with UV radiation, by reducing atmospheric oxygen and oxidising (mineralising) the impurities to form environmentally friendly end products. Furthermore, the surface of titanium dioxide can advantageously become superhydrophilic by absorption of UV radiation. The radiation source device advantageously emits electromagnetic radiation with a wavelength in a range of from 380 nm to 315 nm. Such radiation is also referred to as so-called UV-A radiation. However, the use of UV-B radiation (315 nm-280 nm) and UV-C radiation (280 nm-100 nm) would also be conceivable. With an advantageous use of UV-C radiation, this radiation would already have a corresponding effect on the air or air flow. In particular, the short-wave UV radiation has a strong bactericidal effect. It is absorbed by the DNA of the microorganisms and destroys their structure there. The living cells are inactivated in this way.

According to a further advantageous embodiment, the at least one radiation source is arranged on a carrier device. The carrier device is advantageously plate-like. The carrier device is preferably designed as a printed circuit board (PCB). The carrier device is preferably arranged substantially opposite the photocatalysis device. The passage channel for the air or air flow is advantageously provided between the carrier device and the photocatalysis device. Such an arrangement allows optimal irradiation of the photocatalysis surface with the electromagnetic radiation. Furthermore, optimal contact of the photocatalysis surface with the air flow can be ensured.

According to a further advantageous embodiment, the air treatment apparatus comprises a housing with at least one air inlet opening and at least one air outlet opening. The air flow preferably flows into the air treatment apparatus through the at least one air inlet opening and out of the air treatment apparatus through the at least one air outlet opening. The air flow preferably flows from the at least one air outlet opening into the container device. The advantageous removal of a certain amount of air and the advantageous supply of a certain amount of air creates a circulation of air in the container device. By virtue of such an advantageous circulation of air, a large part of the air in the container device, or substantially all of the air in the container device, is successively supplied to the air treatment apparatus. The at least one air flow device advantageously generates a negative pressure at the air inlet opening. This negative pressure can preferably be used to generate an air flow into or through the at least one air inlet opening. Advantageously, a corresponding overpressure is generated by the air flow device at the at least one air outlet opening. The at least one air flow device preferably conveys the air flow further to the treatment device, through said device, and then through the at least one air outlet opening back into the container device. The air flow device advantageously comprises a rotor or a fan driven by a motor, in particular an electric motor.

According to a further advantageous embodiment, the closure device comprises at least one closure element which, in a closed position, sealingly closes the at least one air inlet opening and/or the at least one air outlet opening. The closure device preferably comprises only one closure element which, in a closed position, sealingly closes the at least one air inlet opening and the at least one air outlet opening. Alternatively, the closure device comprises two closure elements which, in a closed position, each sealingly close the at least one air inlet opening or the at least one air outlet opening. The at least one closure element can preferably be moved from a closed position to an open position. It is also advantageous for the closure element to be movable from the open position to the closed position. In the open position of the at least one closure element, the air flow can preferably enter the at least one air inlet opening and exit through the at least one air outlet opening. The closure device preferably comprises at least one drive device which drives the at least one closure element. The movement is thus preferably carried out by means of the drive device. The drive device advantageously comprises an electric motor. It is of course also conceivable for the closure element to be moved into intermediate positions. Such intermediate positions can limit the entering and/or exiting air flow, for example, by partially covering the at least one air inlet or air outlet opening, for example. The air flow or the amount of air can thus advantageously be controlled.

According to a further advantageous embodiment, the at least one closure element is plate-like. Preferably, only one plate-like closure element is provided. The at least one closure element can preferably be moved in a height direction Z relative to the housing of the air treatment apparatus. When moving to the open position, the at least one closure element can preferably be moved away from the housing of the air treatment apparatus in a height direction Z. When moving to the closed position, the at least one closure element can preferably be moved in a height direction Z towards the housing of the air treatment apparatus. In the open position, the air flow advantageously flows between the housing of the air treatment apparatus and an inner surface of the at least one closure element to the at least one air inlet opening. For this purpose, the drive device could advantageously be designed as a linear drive and/or a spindle drive and/or an actuator.

According to a further advantageous embodiment, the at least one closure element is rotatably arranged on the housing of the air treatment apparatus. Preferably, only one closure element is rotatably arranged on the housing of the air treatment apparatus. In the open position 13b, at least one opening in the at least one closure element is advantageously aligned with at least one opening in the housing, so that an air flow can pass through. The term "align" means that the respective at least one openings are aligned with one another in such a way that the air flow can pass through. In the closed position, the at least one openings are rotated relative to one another in such a way that no air flow can pass through. Accordingly, the at least one opening in the housing would be closed by a portion of the closure element. The at least one opening in the closure element would be closed by a portion of the housing. In the open position, the at least one air inlet opening and the at least one air outlet opening are each advantageously aligned with an opening in the at least one closure element. The air flow thus advantageously passes through at least one first opening in the at least one closure element and through the at least one air inlet opening into the air treatment apparatus. Furthermore, it is advantageous for the air flow to exit from the at least one air outlet opening and at least one second opening in the at least one closure element into the container device. In the closed position, the at least one air inlet opening and the at least one air outlet opening are advantageously sealingly covered by the closure element. For this purpose, the drive device could be designed as a rotary drive.

The present object of the invention is also achieved by a domestic appliance comprising at least one air treatment apparatus according to any of the embodiments described above. The domestic appliance can be equipped with all the features already described above for the air treatment apparatus, individually or in combination with each other, and vice versa.

Such a domestic appliance advantageously comprises a housing and a container device provided therein. The air treatment apparatus can preferably be arranged on or in the housing of the domestic appliance. Such a domestic appliance can advantageously be a dishwasher, a washing machine, a refrigerator, or some other domestic appliance. In the case of a domestic appliance in the form of a dishwasher or a washing machine, the container device is also referred to as a tub. The items to be washed are placed in this tub. During the washing process, a washing liquid in the form of water mixed with a treatment agent is then introduced into the tub.

The domestic appliance may comprise only one air treatment apparatus or a plurality of, for example two, air treatment apparatuses.

According to an advantageous embodiment, at least one control device is provided. The at least one control device can be associated with the domestic appliance or the air treatment apparatus. The control device is advantageously connected by signals to the drive device and/or the air flow device. Preferably, the air treatment apparatus can be activated in a first state and the air treatment apparatus can be deactivated in a second state. Preferably, in the second state, the air treatment apparatus can be sealingly closed off from the container device by means of the closure device. Advantageously, in the second state, the at least one closure element is in the closed position. Likewise, in the second state, the air flow device can be deactivated by the control device. In an embodiment of the domestic appliance in the form of a dishwasher, a washing machine or the like, the washing liquid is introduced into the container device or tub in the second state. Due to the sealing closure of the air treatment apparatus with respect to the container device, the washing liquid cannot penetrate into the air treatment apparatus and damage the treatment device or the air flow device.

The housing of the domestic appliance is preferably designed in a cubic or cuboid shape. The domestic appliance preferably has at least three side walls. The housing can comprise two lateral side walls. The housing can also comprise a rear side wall. Finally, the housing can comprise a front side wall. It is also advantageous for the domestic appliance to have a closure apparatus by means of which the container device can be closed. The closure apparatus can be designed, for example, as a door which is integrated in the front side wall or is provided instead of a front side wall. Operating elements for the user can optionally be provided on the front side wall and/or on the closure apparatus. Such operating elements are program selection switches for a dishwasher, for example. According to a preferred embodiment, the air treatment apparatus is arranged in or on the closure apparatus or the door of the housing of the domestic appliance.

According to a further embodiment, the at least one air treatment apparatus is arranged in or on a side wall of the housing. The at least one air treatment apparatus is advantageously provided on a lateral side wall of the housing. The at least one air treatment apparatus is preferably provided on a rear side wall or rear wall of the housing.

According to a further advantageous embodiment, a first state signal relating to the first state of the air treatment apparatus can be received or generated by the control device. Preferably, a second state signal relating to the second state of the air treatment apparatus can be received or generated by the control device.

According to a further advantageous embodiment, an input device by means of which the first state signal and/or the second state signal can be generated is provided. The input device preferably sends the first state signal and/or the second state signal to the control device. After receiving the first state signal or the second state signal, the control device preferably initiates the first or the second state of the air treatment apparatus. The air treatment apparatus can thus be put into the first state, in which the air treatment apparatus is activated, by a corresponding input by means of or via the input device. The air treatment apparatus can thus also be put into the second state, in which the air treatment apparatus is deactivated, by a corresponding input by means of or via the input device. The input device can preferably be operated manually. Accordingly, the input device can comprise buttons and/or switches and/or a touch screen, for example. It would also be conceivable for the input device to be suitable for processing voice inputs. Alternatively or cumulatively, the input device could also include gesture recognition for inputting commands by means of gestures. The input device can preferably receive the first state signal and/or the second state signal from an external communication device of a user. The connection between the external communication device and the input device is preferably a wireless connection. An external communication device can be a smartphone, a tablet computer, a laptop or a similar device, for example. A corresponding wireless connection can be, for example, an RFID (radio-frequency identification) connection, an NFC (near-field communication) connection, a Wi-Fi connection or a mobile phone connection. Of course, further wireless connections or wired connections can also be used. Accordingly, the user can activate or deactivate the air treatment apparatus in a very convenient way, for example via the smartphone.

The activation or deactivation of the air treatment apparatus can also advantageously take place automatically, however. For this purpose, the control device itself preferably generates the first state signal and/or the second state signal. The corresponding state signals are then processed accordingly by the control device so that the first and the second state are initiated. The at least one control device preferably generates the first state signal and/or the second state signal on the basis of sensor data from a sensor device. The sensor device preferably comprises at least one sensor which detects the loading state in the container device. Such a sensor can be a weight sensor which detects the introduced weight of the items, for example. A sensor in the form of a camera system which can recognise a loading state, for example through image recognition, would also be conceivable. Advantageously, the first state could be triggered or the air treatment apparatus activated when a load is detected, for example in the form of dishes to be cleaned in the case of a dishwasher. Alternatively or cumulatively, the sensor device preferably comprises at least one sensor which detects certain gases in the air in the container device. Such gases may be those which cause an unpleasant odour, for example. Preferably, the first state could be triggered or the air treatment apparatus activated when such a gas is detected. After the removal of the gas, the second state could then be triggered or the air treatment apparatus deactivated. Furthermore, the sensor device could advantageously comprise at least one sensor which detects an opening of the closure apparatus. Thus, the second state could advantageously be triggered or the air treatment apparatus deactivated when the closure apparatus is opened. Advantageously, the first state could be triggered or the air treatment apparatus activated after the closure apparatus has been closed.

The second state signal can preferably also be generated or received when a specific program of the domestic appliance is started, for example when a washing program is started. This can be done using the control device or also a further control device.

According to a further advantageous embodiment, a timer device is provided. Such a timer device can preferably be integrated in the control device or also provided as a further device in the domestic appliance. The first state signal and/or the second state signal can advantageously be generated on the basis of a predetermined point in time or a predetermined time interval. Advantageously, the time at which the first state is activated and the duration of the first state can thus be predetermined.

The control device advantageously comprises a memory device in which particular sequence programs are stored. Such sequence programs can include the sequential actuation of specific devices, such as the air flow device or the treatment device. Likewise, the intensity of the actuation of these devices can advantageously be provided in such a sequence program. The photocatalytic reaction, for example, can be controlled by the advantageous control of the operating current of the radiation source device. Likewise, the air flow speed can be controlled by advantageous actuation of the air flow device.

The present object of the invention is also achieved by a method for controlling a domestic appliance or an air treatment apparatus. The method can be equipped with all the features already described above for the apparatus, individually or in combination with each other, and vice versa.

BRIEF DESCRIPTION OF THE DRAWINGS

Further advantages, aims and properties of the present invention will be explained with reference to the following descriptions of the accompanying drawings. Similar components may have the same reference signs in the various embodiments.

In the drawings:

FIG. 15 is a top view from the front of an air treatment apparatus according to one embodiment;

FIG. 16 is a sectional view of an air treatment apparatus according to one embodiment;

FIG. 17 is a top view from the front of an air treatment apparatus according to one embodiment;

FIG. 18 is a sectional view of an air treatment apparatus according to one embodiment;

FIG. 19 is a sectional view of an air treatment apparatus according to one embodiment;

DETAILED DESCRIPTION

Figure 1:
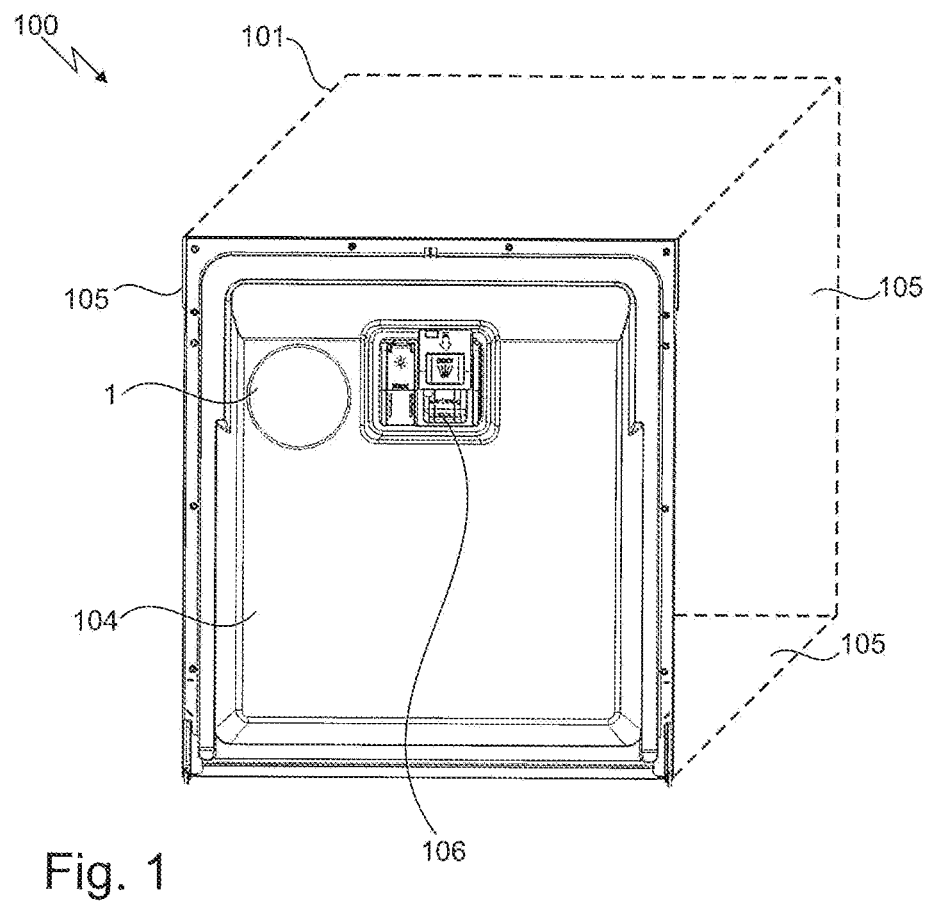
FIG. 1 shows a domestic appliance comprising at least one air treatment apparatus according to one embodiment.

FIGS. 2 to 22 show an air treatment apparatus 1 for a domestic appliance 100, with at least one air flow device 2, 2a, 2b being provided, by means of which an air flow 3 into and/or out of the air treatment apparatus 1 can be generated, the air flow 3 passing through at least one treatment device 4, 4a, 4b, and the air treatment apparatus 1 having a closure device 5 by means of which the air treatment apparatus 1 can be sealingly closed.

FIG. 1 shows a domestic appliance 100 comprising at least one air treatment apparatus 1. The domestic appliance 100 can be a dishwasher, a washing machine, a refrigerator or the like. The domestic appliance 100 comprises a housing 101 and a container device 102 provided therein. The air treatment apparatus 1 can be arranged on or in the housing 101 of the domestic appliance 100. By means of the closure device 5, the air treatment apparatus 1 can be sealingly closed off or separated from the container device 102. Thus, in the case of a washing cycle of the domestic appliance, the interior of the air treatment apparatus 1, in particular the treatment device 4, 4a, 4b, is protected from the washing liquid. Furthermore, by means of the at least one air flow device 2, 2a, 2b, an air flow 3 from and/or into the container device 102 can be generated. Accordingly, the air in the container device 102 can be treated, cleaned or disinfected.

The air treatment apparatus 1 extends along a height axis Z, a longitudinal axis X and a width axis Y. The air treatment apparatus 1 comprises a housing 10 with at least one air inlet opening 11 and at least one air outlet opening 12. The housing 10 is preferably made of a plastic or a metal. The air flow 3 flows into the air treatment apparatus 1 through the at least one air inlet opening 11 and out of the air treatment apparatus 1 through the at least one air outlet opening 12. Accordingly, the air flow 3 flows out of the container device 102 into the at least one air inlet opening 11 and from the at least one air outlet opening 12 into the container device 102. Within the air treatment apparatus 1, the air flow 3 flows through the treatment device 4, 4a, 4b and then to the at least one air outlet opening 12. The air flow 3 entering the container device 102 is thus cleaned or treated. The at least one air flow device 2, 2a, 2b generates a negative pressure at the at least one air inlet opening 11, by means of which pressure the air flow 3 into the at least one air inlet opening 11 can be generated. Correspondingly, an overpressure is generated at the at least one air outlet opening 12. The closure device 5 comprises at least one closure element 13 which, in a closed position 13a, sealingly closes the at least one air inlet opening 11 and/or the at least one air outlet opening 12. The at least one closure element 13 can be moved from a closed position 13a to an open position 13b and vice versa. In the closed position 13a, the at least one air inlet opening 11 and the at least one air outlet opening 12 are sealingly closed. The closure device 5 comprises at least one drive device 14 which drives the at least one closure element 13.

FIGS. 2 to 8 show an embodiment which comprises two air flow devices 2, 2a, 2b. Each of the air flow devices 2, 2a, 2b is fluidically connected to a treatment device 4, 4a, 4b so that the generated air flow 3 passes from the respective air flow devices 2, 2a, 2b to the treatment device 4, 4a, 4b. This is shown for example in FIG. 8 with an arrow for the air flow direction. In this embodiment, the housing 10 is cylindrical, in particular circular cylindrical. However, the present invention is not limited to such a design. Accordingly, other designs of the housing 10 are also conceivable. The housing 10 comprises a front wall 15 in which the two air inlet openings 11 and the two air outlet openings 12 are provided. The air inlet openings 11 and the air outlet openings 12 are designed in the form of slots in the front wall 15. The air flow devices 2, 2a, 2b each comprise a rotor or a fan which is driven by an electric motor and is arranged along the height axis Z behind an air inlet opening 11 in each case or behind the front wall 15. The treatment devices 4, 4a, 4b are also arranged along the height axis Z behind an air outlet opening 11 or behind the front wall 15.

The at least one closure element 13 is plate-like and can be moved in a height direction Z relative to the housing 10 of the air treatment apparatus 1. In the embodiment according to FIGS. 2 to 8, the closure element 13 is substantially circular. This is shown by way of example in FIG. 4. The closure element 13 comprises a substantially circular, plate-like upper portion 16 which is bordered by a collar portion 17. The collar portion 17 extends along the height axis Z towards the housing 10. A diameter of the closure element 13 is preferably greater than a diameter of the housing 10. In the closed position 13a, which can be seen for example in FIG. 2, the closure element 13 therefore partially surrounds the housing 10 by means of the collar portion 17. A seal 22 against which an inner surface 13c of the closure element 13 rests in the closed position 13a is advantageously provided on the front wall. This seal 22 can extend annularly around the two air inlet openings 11 and the two air outlet openings 12.

The closure element 13 is moved by means of a drive device 14. The drive device 14 comprises a helical gearing 18 which has a threaded spindle 18a which is arranged in an internal thread element 18b provided in the housing 10. The threaded spindle 18a is arranged or fastened on the closure element 13, preferably centrally on the closure element 13. A rotational movement of the threaded spindle 18a is converted into a linear movement of the closure element 13 along the height axis Z by the helical gearing 18. The threaded spindle 18a is driven by an electric motor (not shown in FIGS. 2 to 8). It would be conceivable for a further power transmission device such as a gearing, a gear train, a belt drive or the like to be provided for the transmission of power between the motor and the threaded spindle 18a.

Figure 2:
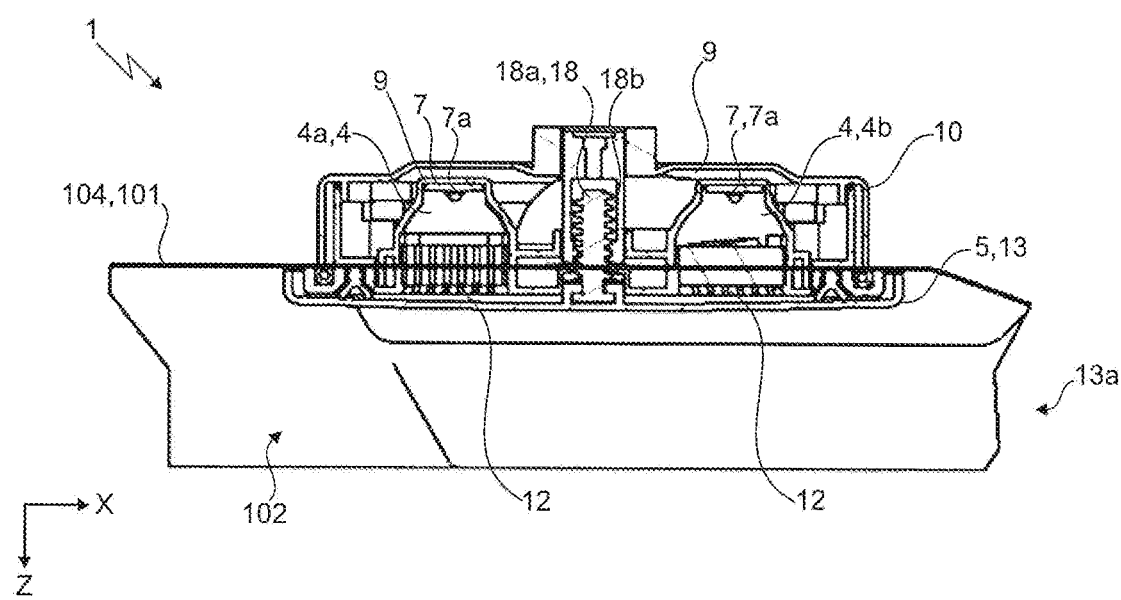
FIG. 2 shows an air treatment apparatus according to one embodiment.
Figure 3:
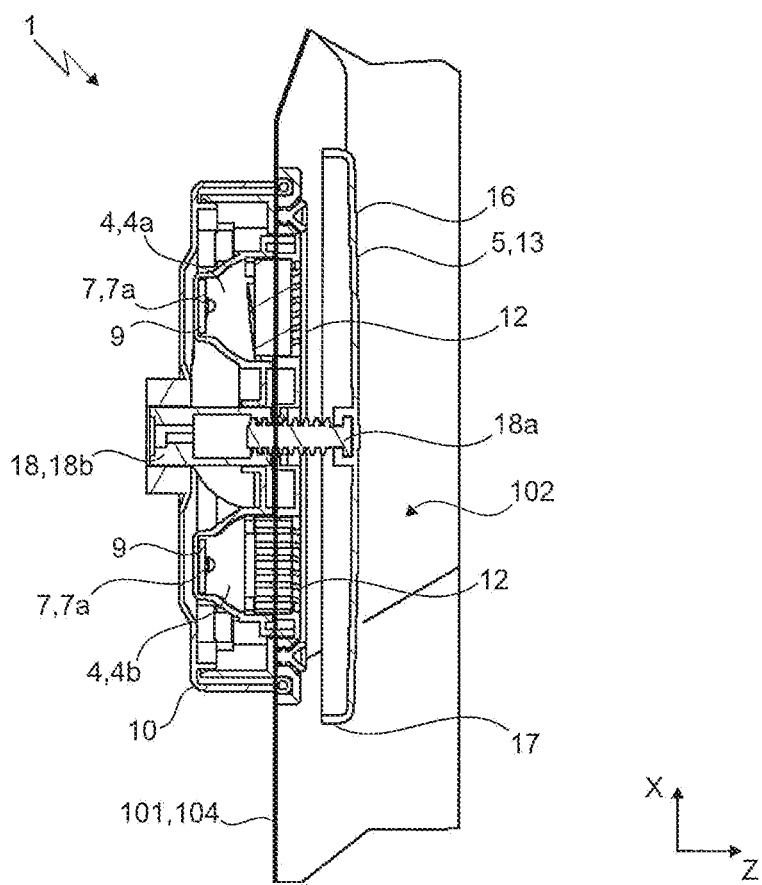
FIG. 3 shows an air treatment apparatus according to one embodiment.

FIGS. 2 and 3 show the air treatment apparatus 1 in the closed position 13a and in the open position 13b, respectively. The housing 101 of the domestic appliance 100 and the corresponding container device 102 are shown.

Figure 4:
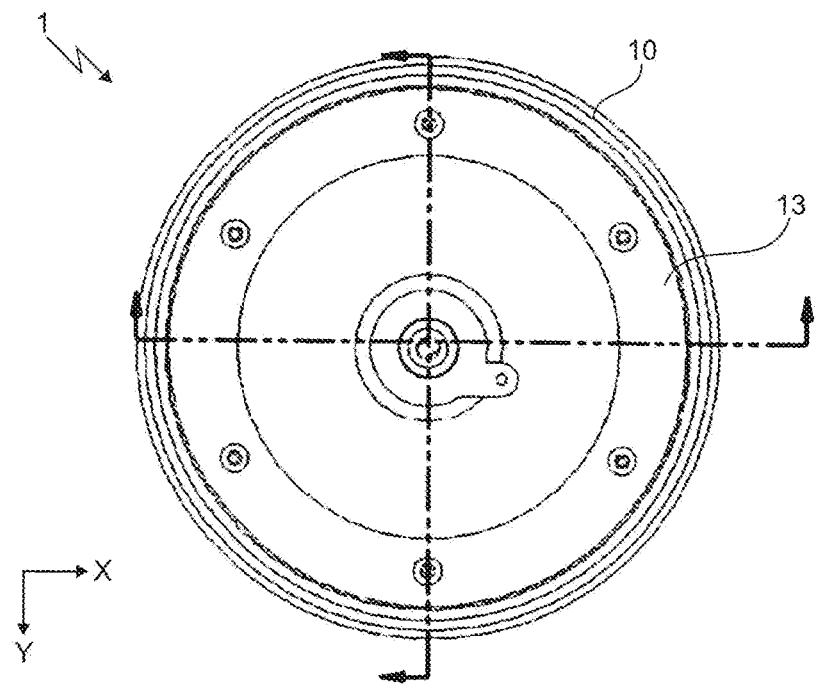
FIG. 4 is a top view of an air treatment apparatus according to one embodiment.
Figure 5:
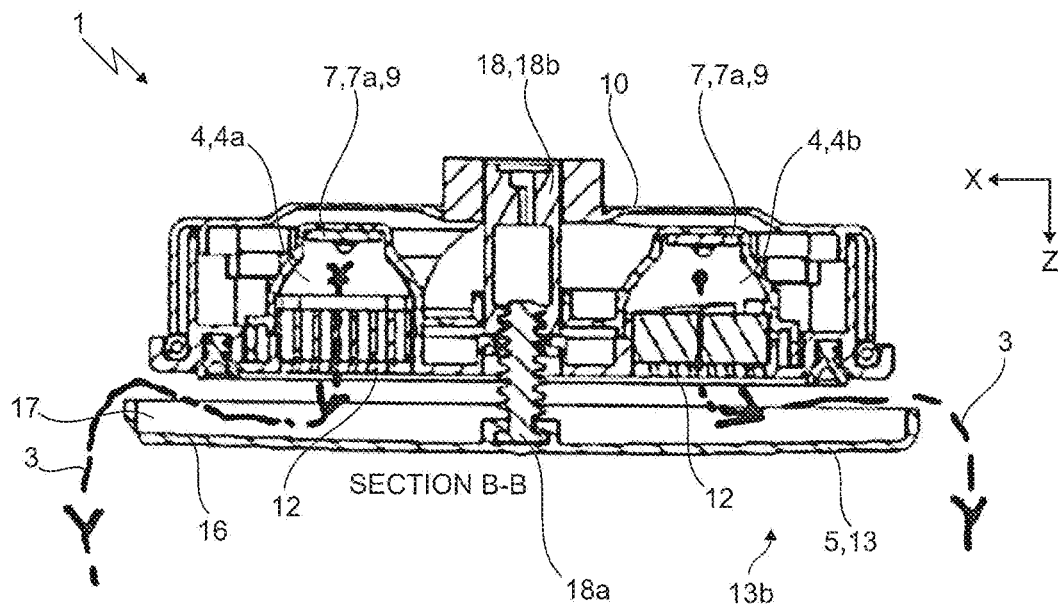
FIG. 5 is a sectional view of an air treatment apparatus according to one embodiment.
Figure 6:
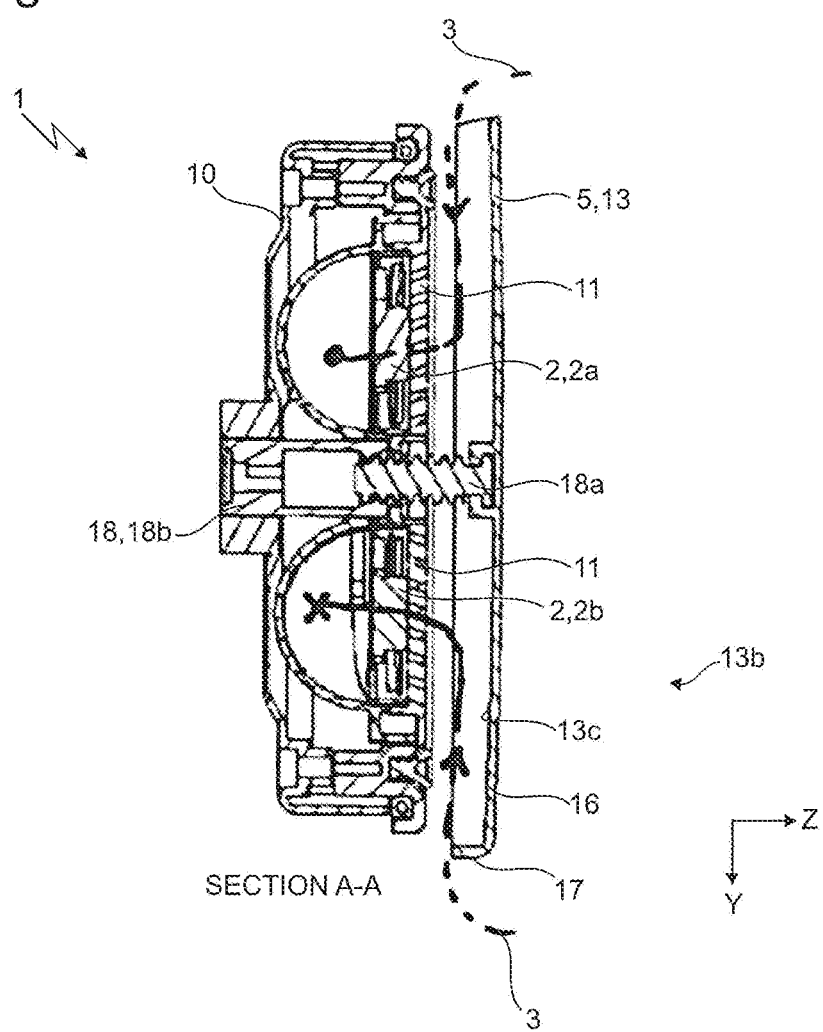
FIG. 6 is a sectional view of an air treatment apparatus according to one embodiment.
Figure 7:
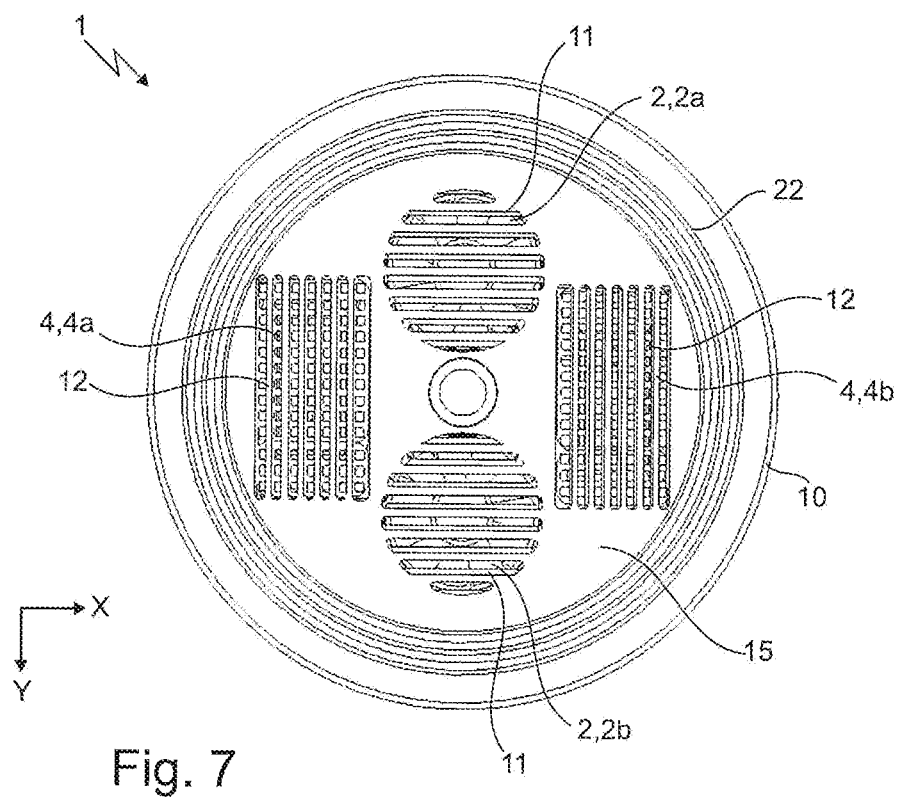
FIG. 7 is a top view of an air treatment apparatus according to one embodiment.
Figure 8:
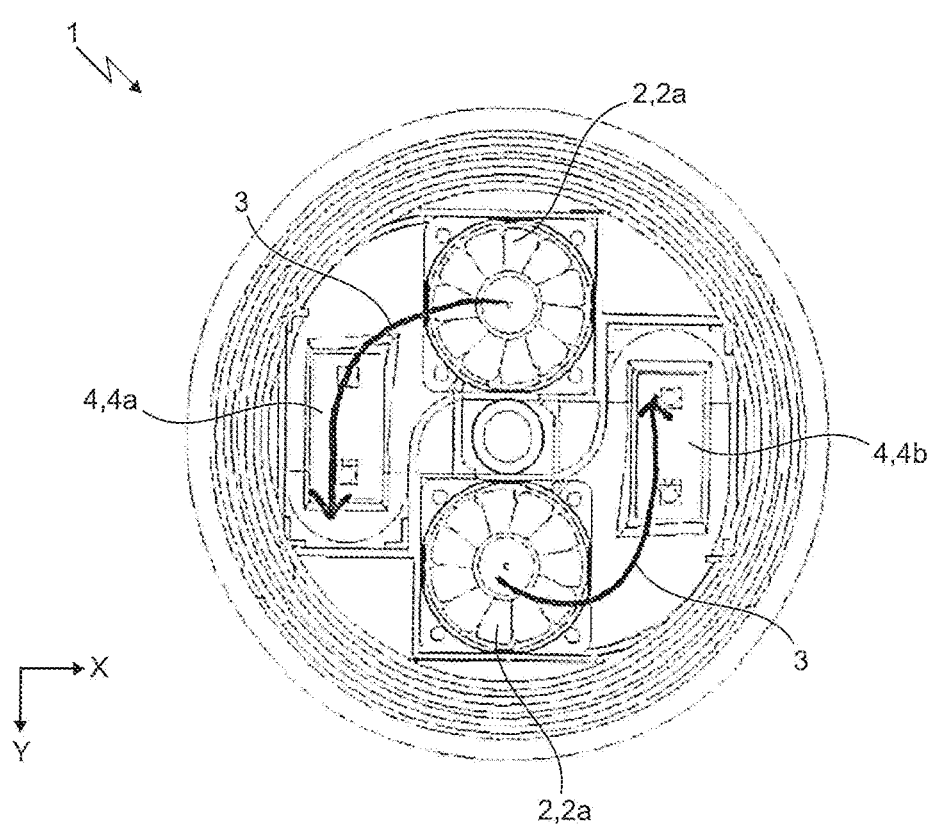
FIG. 8 is a top view of an air treatment apparatus according to one embodiment.

FIGS. 5 and 6 are sectional views along the axes B-B and A-A, respectively, from FIG. 4. In these figures, an arrow is shown for the air flow 3 into and out of the air treatment apparatus 1. In the open position 13b, the air flow 3 flows between the housing 10 of the air treatment apparatus 1 and the inner surface 13c of the closure element 13 to the at least one air inlet opening 11 or the two air inlet openings 11. Likewise, in the open position 13b, the air flow 3 flows away from the at least one air outlet opening 12 or the two air outlet openings 12 and between the housing 10 of the air treatment apparatus 1 and the inner surface 13c of the closure element 13 into the container device 102.

Figure 9:
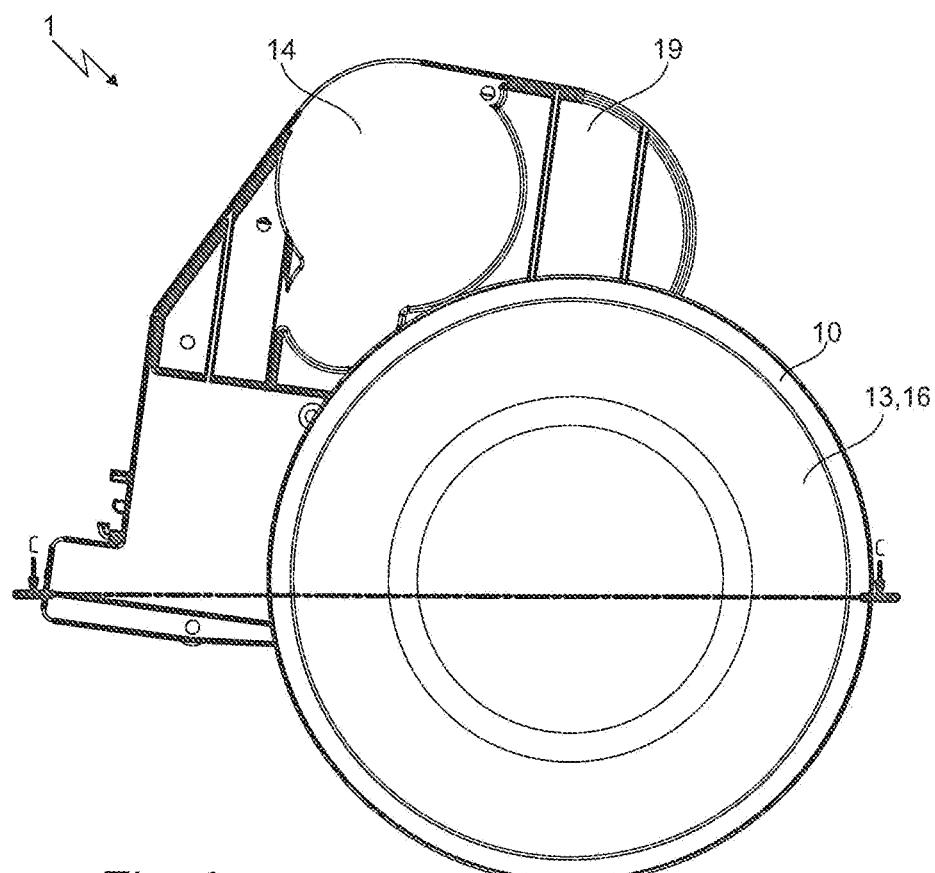
FIG. 9 is a top view of an air treatment apparatus according to one embodiment.
Figure 10:
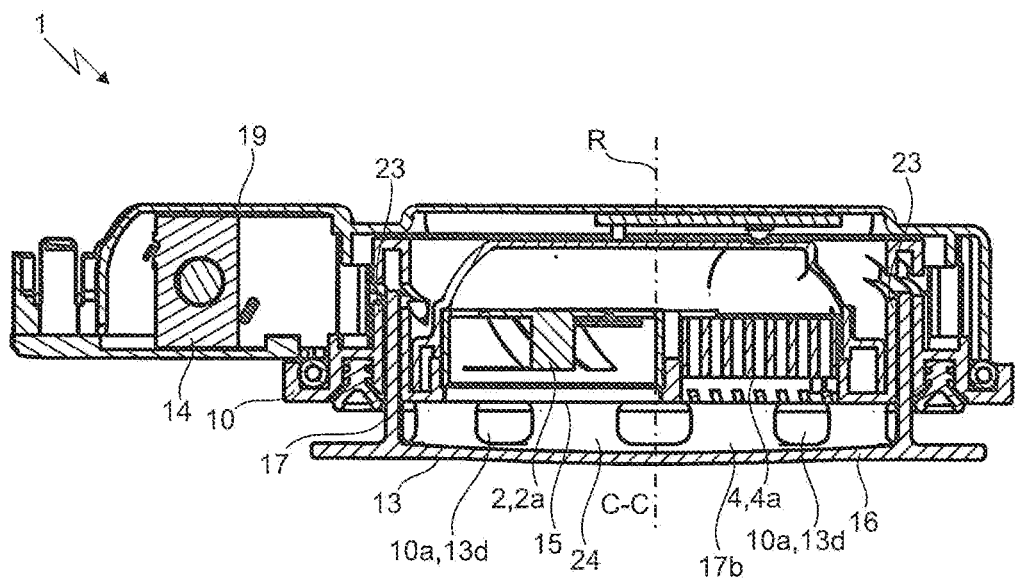
FIG. 10 is a sectional view of an air treatment apparatus according to one embodiment.
Figure 11:
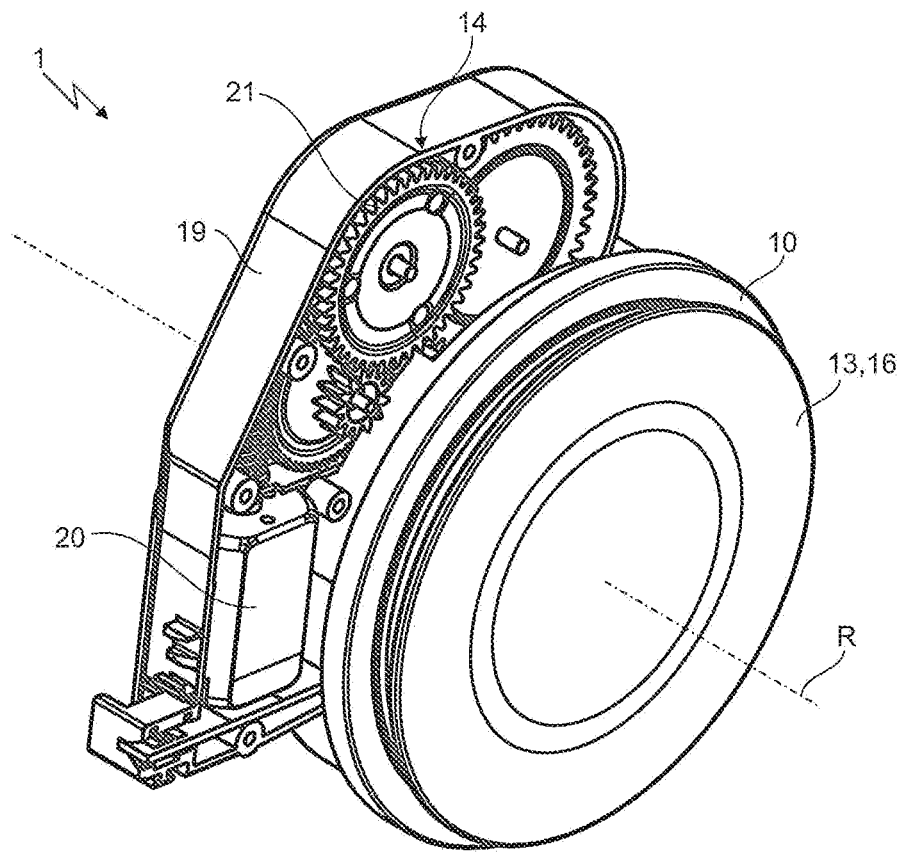
FIG. 11 is a perspective view of an air treatment apparatus according to one embodiment.
Figure 12:
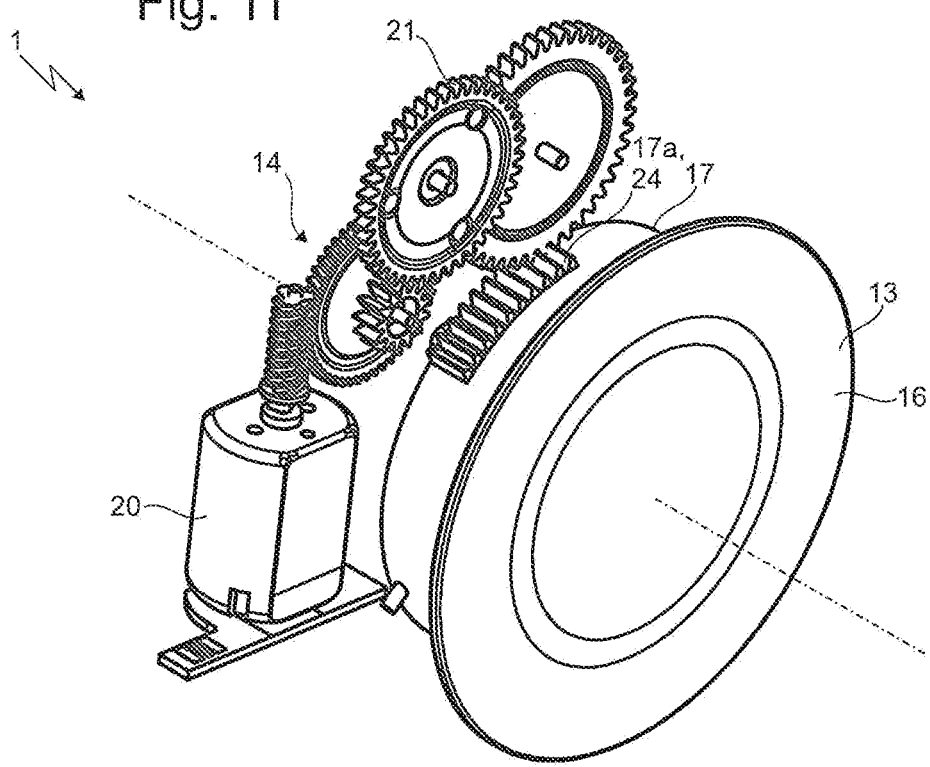
FIG. 12 is a perspective view of an air treatment apparatus according to one embodiment.

FIGS. 9 to 12 show a further embodiment of the air treatment apparatus 1. This embodiment is substantially the same as the embodiment according to FIGS. 2 to 8. Accordingly, two air flow devices 2, 2a, 2b and two treatment devices 4, 4a, 4b are also provided. Furthermore, a housing 10 is provided which is cylindrical, preferably circular cylindrical. FIGS. 9 to 12 also show an additional housing 19 which is arranged on the housing 10 or is designed so as to be integral or in one piece with the housing 10. A top view of such a housing is shown in FIG. 9. FIG. 10 shows a sectional view along the axis C-C in FIG. 9. The drive device 14 is at least partially arranged in the additional housing 19. The drive device 14 comprises a motor 20, preferably an electric motor, and a power transmission device 21 in the form of a gear train. A helical gearing 18 or the threaded spindle 18a, as described for FIGS. 2 to 8, could be driven by such a gear train 21. According to the embodiment in FIGS. 9 to 12, a closure element 13 which is rotatably arranged on the housing 10 is provided. The closure element 13 is cup-shaped and comprises a substantially circular, plate-like upper portion 16 which is bordered by a collar portion 17. The collar portion 17 extends along the height axis Z towards the housing 10. The collar portion 17 is at least partially arranged in a receptacle 23 of the housing 10 so as to be rotatable about an axis of rotation R. In a lower region 17a of the collar portion 17 there is a toothed ring portion 24 which is in engagement with the power transmission device 21 in the form of a gear train of the drive device 14. The closure element 13 can thus be rotated about the axis of rotation R by the drive device 14.

At least one opening 13d, preferably a plurality of openings 13d, of the closure element 13 is provided in an upper region 17b. The housing 10 has a front wall 15 designed in accordance with FIGS. 7 and 8. In this embodiment, however, a collar element 24 is arranged on the front wall 15 or is designed so as to be integral or in one piece therewith. This collar element 24 annularly surrounds the air inlet openings 11 and the air outlet openings 12. The collar element 24 can preferably abut an inner surface 13c of the upper portion 16 of the closure element. A free space is present between the front wall 15 and the upper portion 16 of the closure element 13. At least one opening 10a of the housing 10 is provided in the collar element 24. A plurality of openings 10a are preferably provided in the collar element 24. In the open position 13b, the at least one opening 13d in the at least one closure element 13 is aligned with at least one opening 10a in the housing 10. Accordingly, the number of openings 10a in the housing 10 advantageously corresponds to the number of openings 13d in the closure element 13. The openings 13d in the closure element 13 are thus aligned in the open position 13b with the openings 10a in the housing 10 in such a way that the air flow 3 can pass through. The air flow 3 then enters the air inlet openings 11. The air flow 3 exiting from the air outlet openings 12 also passes through openings 10a, 13d in the housing 10 and in the closure element 13 which are aligned with one another. In the closed position 13a, the openings 10a, 13d in the housing 10 and in the closure element 13 are rotated relative to one another in such a way that no air flow 3 can pass through them. Accordingly, the openings 10a in the housing 10 would be closed by a portion of the closure element 13 or the collar portion 17. The openings 13d in the closure element 13 would be closed by a portion of the housing 10 or by the collar element 24. The air inlet openings 11 and the air outlet openings 12 would accordingly be sealingly closed off or separated from the container device.

The described embodiments according to FIGS. 2 to 12 can also be designed in such a way that only one air flow device 2 and only one treatment device 4 are provided. Likewise, more than two air flow devices 2 and treatment devices 4 can be provided.

Figure 14:
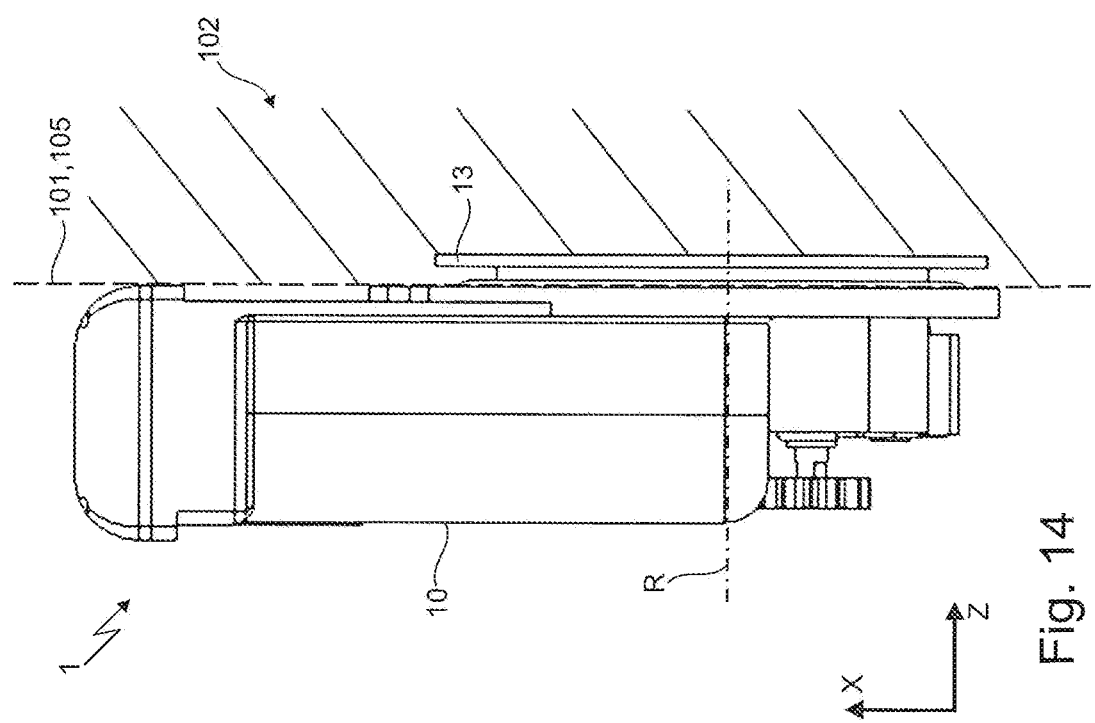
FIG. 14 is a side view of an air treatment apparatus according to one embodiment.
Figure 13:
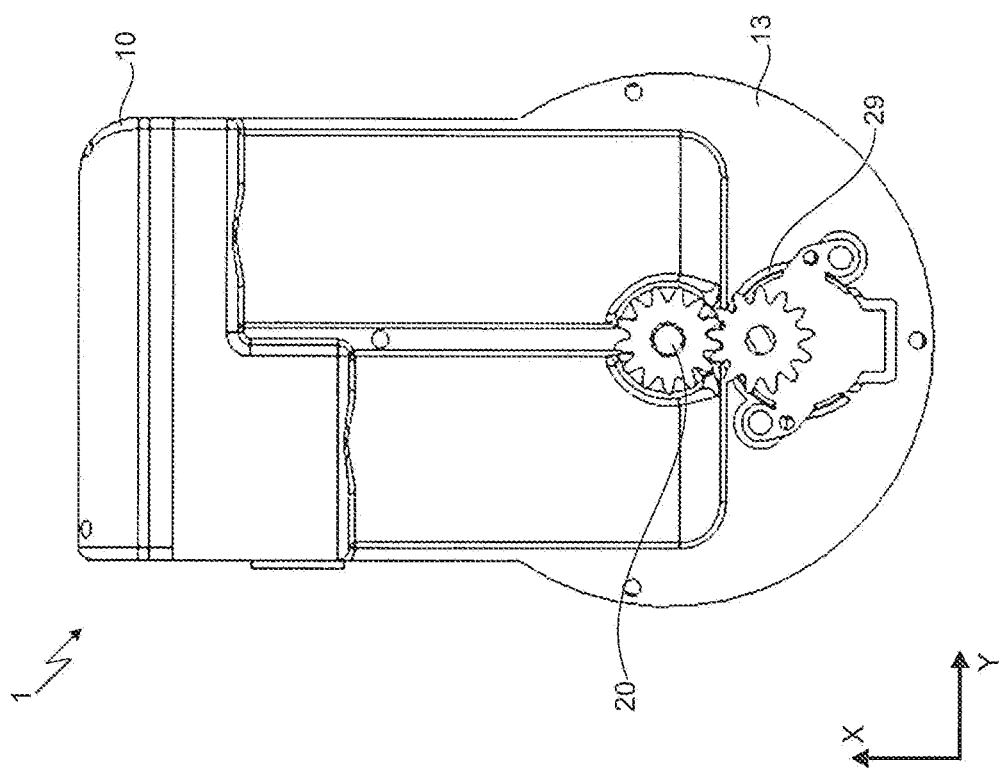
FIG. 13 is a top view from behind of an air treatment apparatus according to one embodiment.
Figure 21:
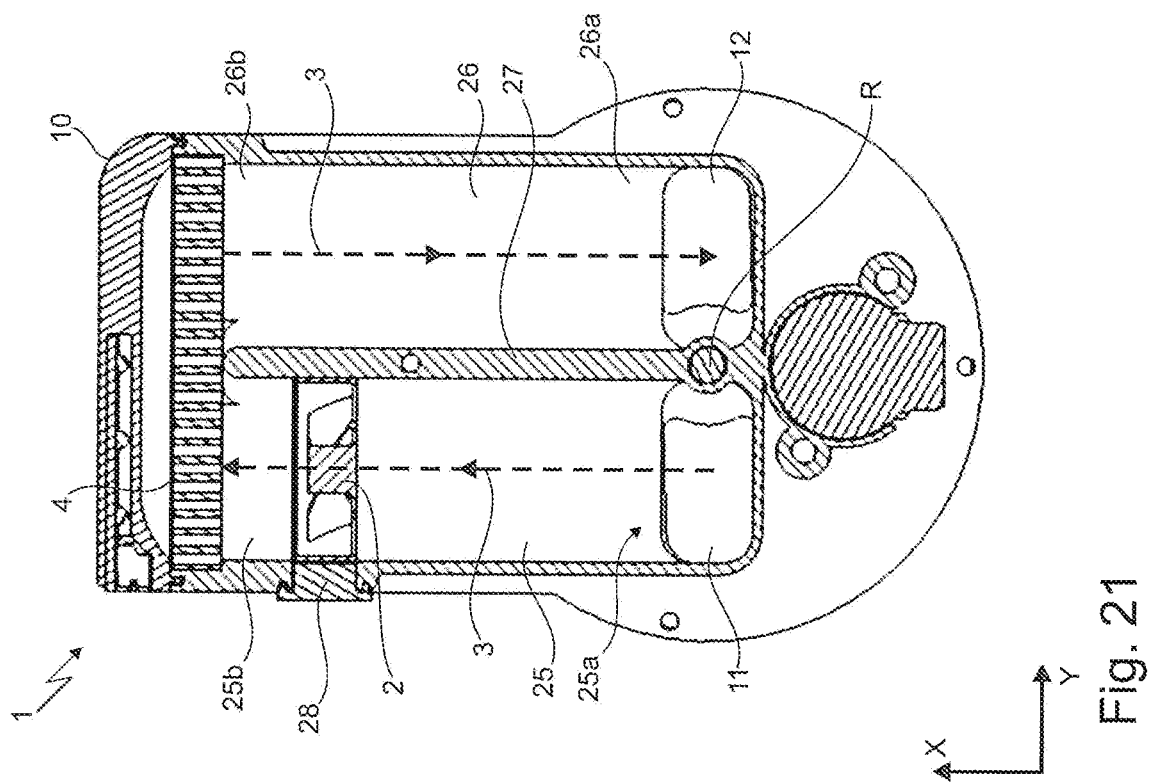
FIG. 21 is a sectional view of an air treatment apparatus according to one embodiment.
Figure 20:
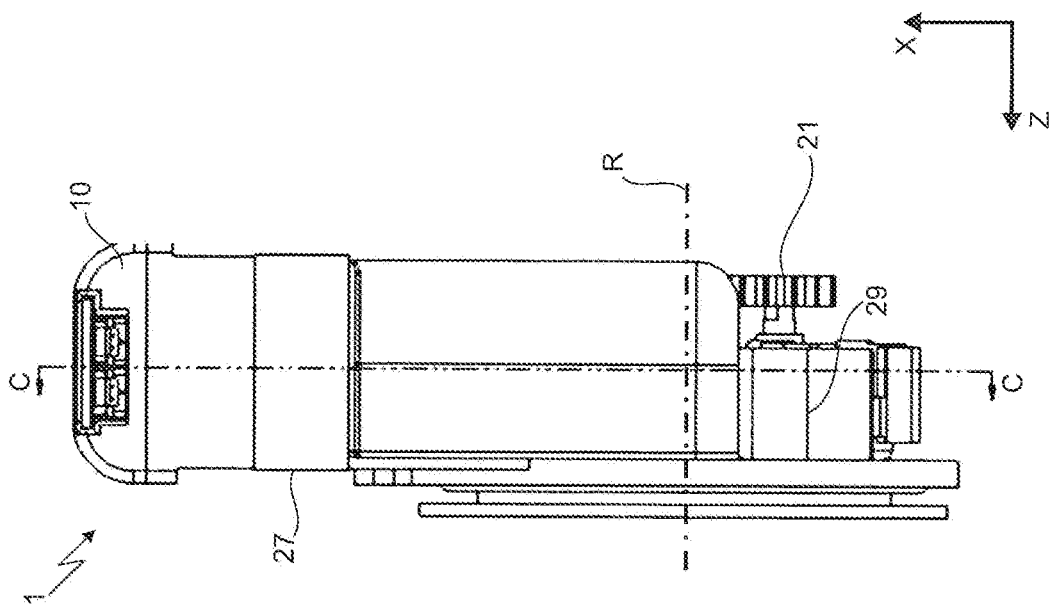
FIG. 20 is a side view of an air treatment apparatus according to one embodiment.

FIGS. 13 to 21 show a further embodiment of the air treatment apparatus 1. FIG. 13 is a rear view and FIGS. 15 and 17 are front views of the air treatment apparatus 1. FIG. 16 is a sectional view along the axis A-A in FIG. 15. FIG. 18 is a sectional view along the axis A-A in FIG. 17. FIG. 19 is a sectional view along the axis B-B in FIG. 17. FIGS. 14 and 20 are side views of the air treatment apparatus 1, with FIG. 14 showing a corresponding installation of the air treatment apparatus 1 in the housing 101 of the domestic appliance 100 and the container device 102 of the domestic appliance 100. Finally, FIG. 21 shows a sectional view along the axis A-A in FIG. 20. The functional principle of the air treatment apparatus 1 according to this embodiment corresponds substantially to that of the embodiments described above. In the following, only the differences from the previously described embodiments are mentioned.

The housing 10 of the air treatment apparatus 1 is substantially cuboid and comprises only one air inlet opening 11 and one air outlet opening 12. The housing 10 is divided into two chamber elements 25, 26. This can be seen in FIGS. 16, 18, 19 and 21. The air inlet opening 11 is arranged in a lower region 25a of the first chamber element 25. The air outlet opening 12 is arranged in a lower region 26a of the second chamber element 26. Furthermore, a partition wall 27 is provided which partially separates the two chamber elements 25, 26 from one another. The partition wall extends from the lower regions 25a, 26a along the longitudinal axis X and ends in the upper regions 25b, 26b of the chamber elements 25, 26. In the upper regions 25b, 26b of the chamber elements 25, 26, the treatment device 4 extends along the width axis Y substantially over both chamber elements 25, 26. In the first chamber element 25, an air flow device 2 is provided which generates a negative pressure at the air inlet opening 11, so that an air flow 3 flows into the first chamber element 25. The air flow 3 flows on to the treatment device 4, through it and into the second chamber element 26. The treated air flow 3 then flows from the second chamber element 26 out of the air outlet opening 12. This is shown in FIGS. 18, 19 and 21 by a corresponding arrow. There is thus a fluidic connection between the first chamber element 25 and the second chamber element 26 only via the treatment device 4. The air inlet opening 11 and the air outlet opening 12 are arranged on an elongate side wall 27 which extends along the longitudinal axis X. The air inlet opening 11 and the air outlet opening 12 are oriented along the height axis Z in this case. The air flow device 2 comprises a rotor or a fan which is driven by a motor and is oriented along the longitudinal axis X. The air flow 3 will thus flow in an arc shape in the lower region 25a of the first chamber element 25. FIG. 21 shows that the air flow device 2 is integrated in an insertion element 28. This insertion element 28 can be arranged on the housing 10 by means of a form-fitting and/or force-locking connection. It can therefore also be easily removed for maintenance purposes, for example for cleaning. The insertion element 28 or the air flow device 2 substantially fill the space available in the first chamber element 25 along the width axis Y, so that the air flow 3 substantially passes through the air flow device 2.

According to this embodiment, the closure element 13 is substantially plate-like with a substantially circular base. The closure element 13 is arranged on a lower region of the housing 10 so as to be rotatable about an axis of rotation R. The closure element 13 is arranged on the housing 10 along the height axis Z. The closure element 13 comprises two diametrically opposed openings 13d arranged on the front wall 19. The air inlet opening 11 and the air outlet opening 12 are at the same height along the longitudinal axis X. In the open position 13b, the air inlet opening 11 is aligned with an opening 13d in the closure element 13 and the air outlet opening 12 is aligned with a further opening 13d in the closure element 13. The openings 13d are arranged in a radially inner region of the front wall 19. An annular region adjoining this region in the radial direction is moved forwards along the height axis Z, so that the front wall 19 is step-shaped. The radially inner region abuts the housing 10 or the side wall 27. The openings 13d in the closure element 13 are thus aligned in the open position 13b with the air inlet opening 11 and the air outlet opening 12 in such a way that the air flow 3 can pass through. In the closed position 13a, the openings 13d in the closure element 13 are rotated relative to the air inlet opening 11 and the air outlet opening 12 in such a way that no air flow 3 can pass through them. Accordingly, the openings 13d in the closure element 13 would be sealingly closed by a portion of the housing 10. Likewise, the air inlet opening 11 and the air outlet opening 12 would be sealingly closed by a portion of the closure element 13. The air inlet opening 11 and the air outlet opening 12 would accordingly be sealingly closed off or separated from the container device 102.

The closure element 13 is also driven by a drive device 14. The drive device 14 comprises a motor 20, preferably an electric motor, which is arranged in the housing 10. The motor 20 drives a gearing 21 having two gear wheels, as shown in FIG. 13. This gearing 21 drives a further gearing 29, which in turn drives the rotation of the closure element about the axis of rotation R. The further gearing 29 is arranged along the longitudinal axis X below the axis of rotation R and is advantageously designed as an epicyclic gearing.

The embodiments according to FIGS. 13 to 21 can be designed in such a way that a plurality of air flow devices 2 and treatment devices 4 are provided.

Figure 22:
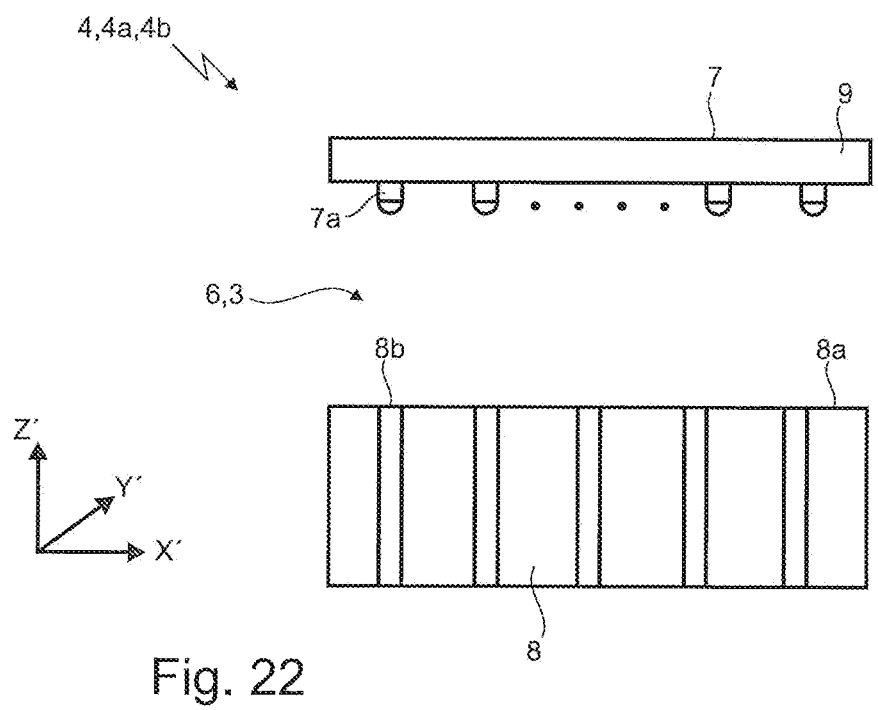
FIG. 22 shows a basic outline of a treatment device according to one embodiment.

FIG. 22 schematically shows a treatment device 4, 4a, 4b.

The treatment device 4, 4a, 4b extends along a height axis Z', a width axis Y', and a longitudinal axis X'. The treatment device 4, 4a, 4b comprises a passage channel 6 for the air flow 3, a radiation source device 7 and a photocatalysis device 8. The radiation source device 7 emits electromagnetic radiation. The photocatalysis device 8 can be exposed to at least part of the electromagnetic radiation to produce a photocatalytic reaction. The photocatalysis device 8 comprises a photocatalysis surface 8a which comprises at least one photocatalytic material. The photocatalytic material is a semiconductor, preferably titanium(IV) oxide, TiO2. The photocatalysis surface 8a comprises regions 8b having the photocatalytic material. However, other designs of the photocatalysis surface 8a are also conceivable. When using titanium dioxide, it is advantageous for the radiation source device 7 to emit electromagnetic radiation with a wavelength of less than 400 nm, preferably in a range of from 380 nm to 315 nm. The radiation source device 7 comprises at least one radiation source 7a, the at least one radiation source 7a being a light-emitting diode (LED) or a UV LED. The radiation source device 7 comprises a large number of radiation sources 7a with a total number $N_{tot}$ of radiation sources 7a. The at least one radiation source 7a is arranged on a carrier device 9. The carrier device 9 is substantially plate-like and is arranged substantially opposite the photocatalysis device 8. The passage channel 6 for the air flow 3 is provided between the carrier device 9 and the photocatalysis device 8.

The carrier device 9 extends in a plane which is spanned by the width axis Y' and the longitudinal axis X'. This photocatalysis surface 8a also extends in a plane which is spanned by the width axis Y' and the longitudinal axis X'. The radiation source device 7, or the carrier device 9 with the radiation sources 7a, is spaced apart from the photocatalysis device 8 or the photocatalysis surface 8a along the height axis Z'.

A domestic appliance 100 is shown in FIG. 1. The housing 101 of the domestic appliance 100 can comprise a closure apparatus 104, for example a door, by means of which the container device 102 can be closed. At least one air treatment apparatus 1 can be arranged in or on the closure apparatus 104. In particular, the embodiments according to FIGS. 2 to 12 and 13 to 21 are particularly suitable for an arrangement in or on the closure apparatus 104.

The domestic appliance 100 can be substantially cubic or cuboid and can comprise two lateral side walls 105a and a rear side wall 105b or also a rear wall, which is preferably opposite the closure apparatus 104. Finally, the housing can comprise a front side wall 105. The closure apparatus 104 can be designed, for example, as a door which is integrated in the front side wall 105 or is provided instead of a front side wall 105. Operating elements for the user can optionally be provided on the front side wall and/or on the closure apparatus 104. Such operating elements are program selection switches for a dishwasher, for example.

The at least one air treatment apparatus 1 can be arranged in or on a side wall 105 of the housing 101. The air treatment apparatus 1 can thus be arranged in or on a lateral side wall 105a or a rear side wall 105b. In particular, the embodiments according to FIGS. 13 to 21 are particularly suitable for an arrangement in or on a side wall 105, 105a, 105b.

Figure 23:
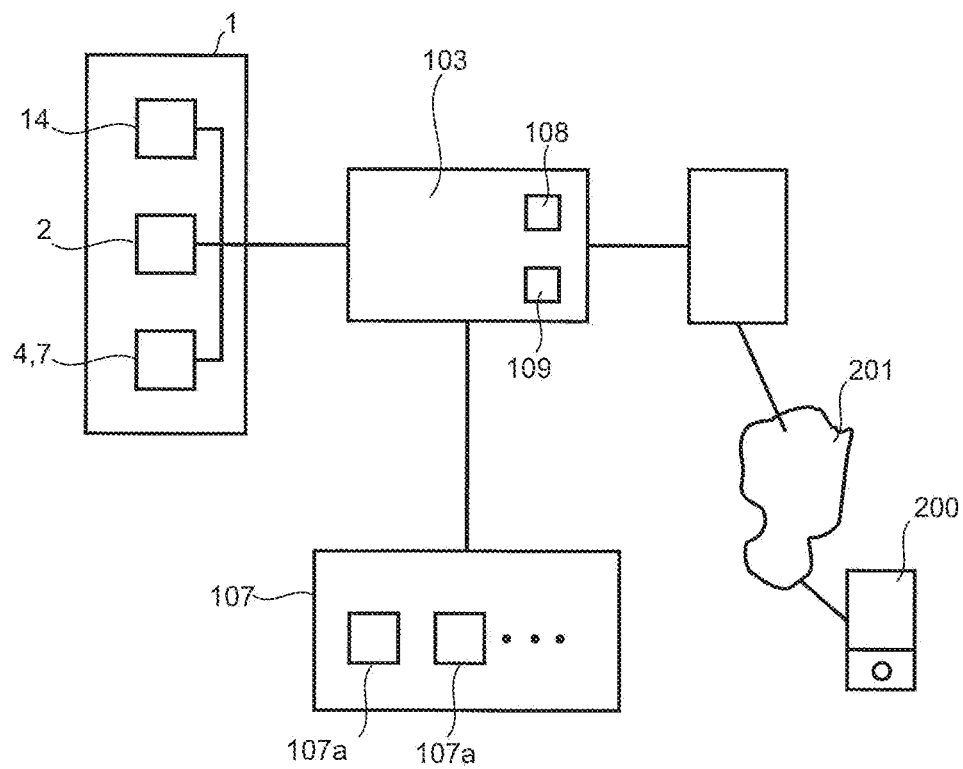
FIG. 23 is a basic circuit diagram for a domestic appliance according to one embodiment.

FIG. 23 is a basic circuit diagram for a domestic appliance 100 comprising at least one air treatment apparatus 1. Accordingly, a control device 103 is provided which can be associated with the domestic appliance or the air treatment apparatus 1. The control device 103 is connected by signals to the air treatment apparatus 1 or the drive device 14, the air flow device 2, the treatment device 4, 4a, 4b, and in particular the radiation source device 7. A first state signal relating to the first state of the air treatment apparatus 1 can be received or generated by the control device 103. A second state signal relating to the second state of the air treatment apparatus 1 can also be received or generated by the control device 103. The air treatment apparatus 1 can be activated in a first state and the air treatment apparatus 1 can be deactivated in a second state. In the second state, the air treatment apparatus 1 can be sealingly closed off from the container device 102 by means of the closure device. In the second state, the at least one closure element 13 is in the closed position 13a. Likewise, in the second state, the air flow device 2 can be deactivated by the control device 103. In an embodiment of the domestic appliance 100 in the form of a dishwasher, a washing machine or the like, the washing liquid is introduced into the container device 102 or tub in the second state. Due to the sealing closure of the air treatment apparatus 1 with respect to the container device 102, the washing liquid cannot penetrate into the air treatment apparatus 1 and damage the treatment device 4 or the air flow device 2.

The control device 103 is connected by signals to at least one input device 106 by means of which the first state signal and/or the second state signal can be generated. The input device 106 sends the first state signal and/or the second state signal to the at least one control device 103, whereupon said control device initiates the first or the second state of the air treatment apparatus 1. The air treatment apparatus 1 can thus be put into the first state, in which the air treatment apparatus 1 is activated, by a corresponding input by means of or via the input device 106. The air treatment apparatus 1 can also be put into the second state, in which the air treatment apparatus 1 is deactivated, by a corresponding input by means of or via the input device 106. The input device 106 can preferably be operated manually. Accordingly, the input device 106 can comprise buttons and/or switches and/or a touch screen, for example. The input device 106 can preferably receive the first state signal and/or the second state signal from an external communication device 200 of a user. The connection between the external communication device and the input device is preferably a wireless connection 201. An external communication device 200 can be a smartphone, a tablet computer, a laptop or a similar device, for example. A corresponding wireless connection 201 can be, for example, an RFID (radio-frequency identification) connection, an NFC (near-field communication) connection, a Wi-Fi connection or a mobile phone connection. Of course, further wireless connections or wired connections can also be used.

The activation or deactivation of the air treatment apparatus 1 can also advantageously take place automatically, however. For this purpose, the control device 103 itself preferably generates the first state signal and/or the second state signal. The corresponding state signals are then processed accordingly by the control device 103 so that the first and the second state are initiated. The at least one control device 103 preferably generates the first state signal and/or the second state signal on the basis of sensor data from a sensor device 107. The sensor device 107 can comprise at least one sensor 107a which detects the loading state in the container device 102. Such a sensor 107a can be a weight sensor which detects the introduced weight of the items, for example. A sensor 107a in the form of a camera system which can recognise a loading state, for example through image recognition, would also be conceivable. Advantageously, the first state could be triggered or the air treatment apparatus 1 activated when a load is detected, for example in the form of dishes to be cleaned in the case of a dishwasher. Alternatively or cumulatively, the sensor device 107 comprises at least one sensor 107a which detects certain gases in the air in the container device 102. Such gases may be those which cause an unpleasant odour, for example. Preferably, the first state could be triggered or the air treatment apparatus 1 activated when such a gas is detected.

After the removal of the gas, the second state could then be triggered or the air treatment apparatus 1 deactivated. Furthermore, the sensor device 107 could comprise at least one sensor 107a which detects an opening of the closure apparatus 104 of the domestic appliance 100. Thus, the second state could be triggered or the air treatment apparatus 1 deactivated when the closure apparatus 104 is opened. The first state could be triggered or the air treatment apparatus 1 activated after the closure apparatus 104 has been closed.

According to a further advantageous embodiment, a timer device 108 is provided. Such a timer device 108 can preferably be integrated in the control device 103 or also provided as a further device in the domestic appliance 100. The first state signal and/or the second state signal can be generated on the basis of a predetermined point in time or a predetermined time interval. The time at which the first state is activated and the duration of the first state can thus be predetermined.

The control device 103 comprises a memory device 109 in which particular sequence programs are stored. Such sequence programs can include the sequential actuation of specific devices, such as the air flow device 2, 2a, 2b or the treatment device 4, 4a, 4b, or the intensity of the actuation of these devices.

In known dishwashers, disinfection is carried out using an appropriate washing program, for example. Corresponding air purification or disinfection of the air in the tub, as in the present invention, has not yet been provided. In a dishwasher, for example, the present air treatment apparatus can also be implemented in an additional pass in the drying program.

The applicant reserves the right to claim all the features disclosed in the application documents as essential to the invention, provided that these are novel, individually or in combination, over the prior art. It is further pointed out that features which in themselves can be advantageous have also been described in the individual drawings. A person skilled in the art will immediately recognise that a particular feature described in one drawing can also be advantageous without adopting further features from this drawing. A person skilled in the art will further recognise that advantages can also result from a combination of a plurality of features shown in individual or in different drawings.

LIST OF REFERENCE SIGNS

1 Air treatment apparatus
2 Air flow device
2a First air flow device
2B Second air flow device
3 Air flow
4 Treatment device
4a First treatment device
4b Second treatment device
5 Closure device
6 Passage channel
7 Radiation source device
8 Photocatalysis device
8a Photocatalysis surface
8b Regions of the photocatalysis surface having the photocatalytic material
9 Carrier device
10 Housing
11 Air inlet opening
12 Air outlet opening
13 Closure element
13a Closed position
13b Open position
13c Inner surface of the closure element
13d Opening in the closure element
14 Drive device
15 Front wall
16 Upper portion of the closure element
17 Collar portion of the closure element
17a Lower region of the closure element
17b Upper region of the closure element
18 Helical gearing
18a Threaded spindle
18b Internal thread element
19 Additional housing
20 Motor
21 Gearing
22 Seal
23 Receptacle
24 Collar element
25 First chamber element
26 Second chamber element
27 Side wall
28 Insertion element
29 Further gearing
100 Domestic appliance
101 Housing
102 Container device
103 Control device
104 Closure apparatus
105 Side wall
105a Lateral side wall
105b Rear side wall
106 Input device
107 Sensor device
107a Sensor
108 Timer device
109 Memory device
200 Communication device
201 Wireless connection
X Longitudinal axis of the air treatment apparatus
Y Width axis of the air treatment apparatus
Z Height axis of the air treatment apparatus
X' Longitudinal axis of the treatment device
Y' Width axis of the treatment device
Z' Height axis of the treatment device
R Axis of rotation

What is claimed is:

1. An air treatment apparatus for a domestic appliance, comprising:
at least one air flow device, by which an air flow into and/or out of the air treatment apparatus can be generated, the air flow passing through at least one treatment device;
a housing having at least one air inlet opening and at least one air outlet opening, the air flow flowing into the air treatment apparatus through the at least one air inlet opening and out of the air treatment apparatus through the at least one air outlet opening; and
a closure device by which the air treatment apparatus can be sealingly closed, comprising:
at least one closure element which, in a closed position, sealingly closes the at least one air inlet opening and the at least one air outlet opening, the at least one closure element being movable between the closed position to an open position by at least one drive device.

2. The air treatment apparatus according to claim 1, wherein the at least one treatment device comprises a passage channel for the air flow, a radiation source device, and a photocatalysis device, wherein the radiation source device emits electromagnetic radiation, wherein the photocatalysis device is exposed to at least part of the electromagnetic radiation to produce a photocatalytic reaction, wherein the photocatalysis device includes a photocatalysis surface that comprises at least one photocatalytic material, wherein the photocatalytic material is a semiconductor, and wherein the photocatalytic material comprises titanium (IV) dioxide, $TiO_2$.

3. The air treatment apparatus according to claim 2, wherein the radiation source device comprises at least one radiation source, wherein the at least one radiation source is a light-emitting diode (LED), the radiation source device emitting electromagnetic radiation with a wavelength of less than 400 nm, and wherein the radiation source device emits electromagnetic radiation with a wavelength in a range of from 380 nm to 315 nm.

4. The air treatment apparatus according to claim 3, wherein the at least one radiation source is arranged on a carrier device, the carrier device being plate-like, the carrier device being arranged substantially opposite to the photocatalysis device, and the passage channel for the air flow being provided between the carrier device and the photocatalysis device.

5. The air treatment apparatus according to claim 1, wherein the at least one air flow device generates a negative pressure at the at least one air inlet opening, and this negative pressure generates an air flow into the at least one air inlet opening.

6. The air treatment apparatus according to claim 5, wherein the at least one closure element is plate-like and is movable in a height direction relative to the housing of the air treatment apparatus, with the air flow flowing between the housing of the air treatment apparatus and an inner surface of the at least one closure element to the at least one air inlet opening in the open position.

7. The air treatment apparatus according to claim 5, wherein the at least one closure element is rotatably arranged on the housing of the air treatment apparatus, with at least one opening in the at least one closure element being aligned with at least one opening in the housing in the open position, and the at least one air inlet opening and the at least one air outlet opening each being aligned with the at least one opening in the at least one closure element in the open position.

8. A domestic appliance comprising:
an air treatment apparatus comprising:
at least one air flow device, by which an air flow into and/or out of the air treatment apparatus can be generated, the air flow passing through at least one treatment device;
a housing having at least one air inlet opening and at least one air outlet opening, the air flow flowing into the air treatment apparatus through the at least one air inlet opening and out of the air treatment apparatus through the at least one air outlet opening; and
a closure device by which the air treatment apparatus can be sealingly closed, comprising:
at least one closure element which, in a closed position, sealingly closes the at least one air inlet opening and the at least one air outlet opening, the at least one closure element being movable between the closed position to an open position by at least one drive device;
a second housing; and
a container device provided therein.

9. The domestic appliance according to claim 8, wherein the second housing of the domestic appliance comprises a closure apparatus by which the container device can be closed, the air treatment apparatus being arranged in or on the closure apparatus and the air treatment apparatus being arranged in or on a side wall of the second housing.

10. The domestic appliance according to claim 8, wherein at least one control device is provided, the air treatment apparatus being activated in a first state and the air treatment apparatus being deactivated in a second state, it being possible to sealingly close off the air treatment apparatus from the container device by means of the closure device in the second state.

11. The domestic appliance according to claim 10, wherein a first state signal relating to the first state of the air treatment apparatus can be received or generated by the at least one control device, with the at least one control device able to receive or generate a second state signal relating to the second state of the air treatment apparatus.

12. The domestic appliance according to claim 11, wherein at least one input device by which the first state signal and/or the second state signal can be generated is provided, the input device sending the first state signal and/or the second state signal to the at least one control device, whereupon the at least one control device initiates the first state or the second state of the air treatment apparatus, and the input device being able to receive the first state signal and/or the second state signal from an external communication device of a user.

13. The domestic appliance according to claim 11, wherein the at least one control device generates the first state signal and/or the second state signal on the basis of sensor data from a sensor device, the sensor device comprising a first sensor that detects a loading state in the container device, a second sensor that detects specific gases in the container device, and a third sensor which detects an opening of the closure device.

14. The domestic appliance according to claim 11, wherein a timer device is provided, and wherein the first state signal and/or the second state signal is generated on the basis of a predetermined point in time or a predetermined time interval.

* * * * *